United States Patent [19]

Gordon

[11] Patent Number: 4,889,120

[45] Date of Patent: Dec. 26, 1989

[54] METHOD FOR THE CONNECTION OF BIOLOGICAL STRUCTURES

[76] Inventor: Robert T. Gordon, 4936 W. Estes, Stokie, Ill. 60077

[21] Appl. No.: 867,023

[22] Filed: May 27, 1986

Related U.S. Application Data

[63] Continuation-in-part of Ser. No. 670,738, Nov. 13, 1984, abandoned.

[51] Int. Cl.$^4$ ............................................. A61B 17/04
[52] U.S. Cl. ..................................... 606/216; 600/10; 606/157
[58] Field of Search .................... 128/1.3, 1.5, 303.1, 128/68.1, 82.1, 334 R, 334 C; 600/10, 21, 12, 13

[56] References Cited

U.S. PATENT DOCUMENTS

| | | | |
|---|---|---|---|
| 3,722,599 | 3/1973 | Robertson et al. | 128/334 R |
| 3,890,953 | 6/1975 | Kraus et al. | 128/1.5 |
| 3,893,462 | 7/1975 | Manning | 600/13 |
| 3,987,795 | 10/1976 | Morrison | 128/303.14 |
| 4,005,699 | 2/1977 | Bucalo | 128/1 R |
| 4,013,063 | 3/1977 | Bucalo | 128/1.3 |
| 4,016,886 | 4/1977 | Doss et al. | 128/399 |
| 4,024,855 | 5/1977 | Bucalo | 128/1.3 |
| 4,057,535 | 11/1977 | Lipatora | 128/335.5 |
| 4,136,683 | 1/1979 | Gordon | 128/1.3 |
| 4,202,337 | 5/1980 | Hien et al. | 128/303.14 |
| 4,323,056 | 6/1982 | Borrelli et al. | 604/28 |
| 4,359,453 | 11/1982 | Gordon | 128/1.1 |
| 4,452,773 | 6/1984 | Molday | 424/1.1 |
| 4,545,368 | 10/1985 | Rand et al. | 128/1.3 |
| 4,587,957 | 5/1986 | Castel | 128/1.5 |
| 4,596,728 | 6/1986 | Yang et al. | 128/334 C |
| 4,610,241 | 9/1986 | Gordon | 128/1.3 |
| 4,641,633 | 2/1987 | Delgado | 600/13 |
| 4,672,951 | 6/1987 | Welch | 128/82.1 |

OTHER PUBLICATIONS

Tumor Imaging with Radioactive Chelates Conjugated to Monoclonal Antibodies, Science, vol. 215, 19 Mar. 1982, pp. 1511–1513.

*Primary Examiner*—C. Fred Rosenbaum
*Assistant Examiner*—Kathleen Daley
*Attorney, Agent, or Firm*—Lalos & Keegan

[57] ABSTRACT

A method of creating connections between blood vessels and other biological structures by the application of electromagnetic energy capable of the generation of heat and biophysical alterations in intracellular particles and particles within the edges of the biological structure as well as within the edges of the biological structure itself. The process allows for the creation of connection between biological structures without damaging the biological structures themselves.

The process comprises introducing minute particles into the edges of the biological structures to be connected. These particles are either intracellular and/or extracellular and can be introduced at the time of connection and/or prior to connection. These particles are suspended in an appropriate solution and are of a size generally having a diameter of approximately 1 micron or less and are of a material with properties such as ferromagnetic, paramagnetic or diamagnetic so as to be inductively heated when subjected to the radiation. The structures are then exposed to a source of electromagnetic radiation to inductively heat the particles sufficient to connect the biological structures without harming the biological structures.

70 Claims, No Drawings

METHOD FOR THE CONNECTION OF BIOLOGICAL STRUCTURES

The present application is a continuation-in-part of application Ser. No. 670,738, filed Nov. 13, 1984, now abandoned, the contents of which are hereby incorporated by reference in their entirety.

The invention relates generally to a process and composition for the connection of biological structures in living tissue. More particularly the present invention relates to method and composition for the connection of biological structures by inductively raising the energy level at the edges of the biological structures without affecting the biological structures involved.

BACKGROUND OF THE INVENTION

There are presently a number of methods and techniques for connecting biological structures. These techniques generally involve suturing the structures together as is the case in vascular surgery, gastrointestinal tract surgery, urological surgery, etc. Attempts have been made to find the ideal suture material since this material acts as a large foreign body and may stimulate fistula formation, necrosis of the wall of the biological structures and a reaction from the tissue itself. Similarly attempts have been made to vary the anastomotic technique using single layer or double layer closure to obtain a better anastomosis.

The realization that the suture technique requires time and produces tissue changes which are long lasting was evident. The length of time of surgery or other procedures is important to the ultimate well being of the patient, concomittantly the quality of the anastomosis is important to the patient's long term future.

Attempts have been made to use stapling devices to join structures. These devices generally evert the tissue edges and staple them with metal pins or staples. These devices have been useful for large structures but have not been of much use for small blood vessels or fine structures.

The use of the laser to join blood vessels has been attempted. Different lasers have been tried. Two major problems exist. The first entails the fact that the laser provides spot fusion and therefore is time consuming since one must go over the entire anastomosis point by point. Secondly since the laser burns from superficial downwards it is difficult to control the energy level properly and often only the outer layers are fused which leads to aneurysm formation in thick vessels. Too deep penetration will burn through the vessel. These two points are major drawbacks to the current use of the laser.

Absorbable devices have been described to unite vessels by everting the tissue and holding them connected (Daniel et al)(Plastic and Reconstructive Surgery, Vol. 74, No. 3. Sept., 1984). However these devices require bulky connections. In addition the device requires a large amount of tissue handling with eversion and crushing of tissue. The device requires time to insert and cannot be used for and to side or side to side anastomosis. This device also in its pull through and eversion of tissue uses up quite a bit of length of the vessel in everting the tissue and can create tension. Tension in an anastomosis is often a cause of problems. This device also cannot handle large size discrepancies between vessels.

A safe and effective method of connecting biological structures has been the goal of investigators for a substantial period of time. Such a technique to be successful must allow for a good biological healing of the connected structures, performed in a very short period of time, connect all depths of the edge of the biological structure evenly, not require spot by spot welding of tissue, avoid tension on the anastomosis, avoid the use of bulky instrumentation in the biological tissue, be capable of use in end to side and side to side anastomosis and be able to handle size discrepancies and unusual anatomy.

The ability to excite particles in biological tissue has been shown (Gordon, et al). The edges of the biological structures will take up the particles by passive means or the particles may be injected. This may be at the time of connection and/or prior to the formation of the connection of the biological structures.

OBJECT OF THE INVENTION

It is therefore the purpose and principal object of the present invention to connect biological structures by generating a temperature and changing biophysical characteristics that will form the connection without affecting the biological structures.

DESCRIPTION OF THE INVENTION

The present invention achieves a precise increment of heat rise and energy change at the edges of the biological structures to form a connection. The term "edges" as used hereinafter shall also include sides of the biological structures.

Inaccordance with the present invention there are found to be a number of approaches that can successfully achieve the end result of forming the biological connection.

In its simplest and broadest aspect the present invention contemplates the introduction into the edges of biological structures a minute particle, such as a ferromagnetic, paramagnetic or diamagnetic material and then subjecting the approximated edges to an alternating electromagnetic field generated by an alternating current or a light source.

The particles which are useful inaccordance with the present invention are those such as the ferromagnetic particles compatible with living tissue. Similarly the paramagnetic or diamagnetic materials that may be useful include the following radioactive isotope labeled albumin, fibringen and cholesterol and any other diamagnetic and paramagnetic materials compatible with living tissues (in addition any electric or magnetic dipole present or capable of being induced within the edge of the biological structure can be utilized). The particle size can vary from no greater than 1 micron to 7-10 microns. Preferably particle size would be less than 1 micron size. Particles of use include the following (R. T. Gordon U.S. Pat. Appl. No. 464,870 and CIP Ser. No. 559,229), both inorganic elements and compounds as well as metal-containing organic compounds. Inorganic elements and compounds particularly well suited, owing to their favorable magnetic parameters, comprise elements, such as dysprosium, erbium, europium, gadolinium, holmium, samarium, terbium, thulium, ytterbium or yttrium and compounds thereof such as dysprosium sulfate, erbium sulfate, europium oxide, europium sulfate, gadolinium oxide, gadolinium sulfate, holmium oxide, samarium sulfate, terbium oxide, terbium sulfate, thulium oxide, ytterbium sulfide, yttrium oxide, yttrium sulfate, yttrium ferrioxide ($Y_3Fe_5O_{12}$) yttrium aluminum oxide ($Y_3Al_5O_{12}$), other dimetallic compounds such as dysprosium-nickel, dysprosium-cobalt, gadolinium-iron, ytterbium-iron, cobalt-samarium, gadolinium-yttrium, and dysprosium-gallium, and actinide series elements and compounds thereof.

Metal-containing organic molecules useful for the application discussed above, comprise particles of iron-dextrans such as FeOOH-dextran or $Fe_3O_4$-dextran complexes and other dextran metal complexes wherein the metal is selected from the group comprising cobalt, zinc, chromium nickel, gallium, platinum, manganese and rare earth metals such as dyprosium, erbium, europium, gadolinium holmium, samarium, terbium, thulium, ytterbium and yttrium, other dimetallic compounds such as dysprosium-nickel, dysprosium-cobalt, gadolinium-iron, ytterbium-iron, cobalt-samarium, gadolinium-yttrium, and hysprosium-gallium, actinide series elements and compounds, ferric ammonium citrate, and various iron transporting and chelating compounds such as enterochelin, hydroxamates, phenolates, ferrichromes, desferri-ferrichromes, ferritin, ferric mycobactins, and iron-sulfur proteins such as ferredoxin and rubredoxin.

Particularly appropriate metal-containing organic structures for use with the present invention are the metalloporphyrins such as etioporphyrins, mesoporphyrins, uroporphyrins, coproporphyrins, protoporphyrins, and dicarboxylic acid containing porphyrins and substituted porphyrins such as tetraphenylporphyrin sulfonate (TPPS). Especially advantageous protoporphyrins comprise hematoporphyrins, chlorophylls, and cytochromes. In addition to the naturally occuring protoporphyrins which possess either iron or magnesium-containing moieties, mixed-metal or di-metal hybrid porphyrins may also be prepared. For example, by substituting an alternative metal for the iron in hematoporphyrin, the advantages of the porphyrin moiety (e.g., in terms of specificity of localization is retained while the unique magnetic properties of the new metal enhance the sensitivity of the substituted molecule. Suitable metals for purposes of substitution comprise cobalt, manganese, zinc, chromium, gallium, nickel, platinum and rare earth series of metals dysprosium, erbium, europium, gadolinium, holmium, samarium, terbium, thulium, ytterbium and ytterium, dimetallic compounds such as dysprosium-nickel, dysprosium-cobalt gadolinium-iron, ytterbium-iron, cobalt-samarium, gadolinium yttrium, dysprosium-gallium and actinide series elements and compounds thereof. The substituted porphyrins are then optionally reacted with dextran to form a metal-containing porphyrin dextran complex in particle form. Suitable porphyrin acceptors comprise any dicarboxylic acid containing porphyrin, such as protoporphyrins (e.g., hematoporphyrins), and the like.

The substitution reaction is carried out in vitro by reacting the desired metal with the desired porphyrin in the presence of the enzyme ferrochelatase (E.C. 4.99.1.1). Reaction conditions as described by Jones and Jones (Biochem. J. 113:507–14 (1969) or Honeybourne, et al, (FEBS Lett.: 98:207-10 (1979) are suitable.

Particularly advantageous particle systems include transferrin-based particle systems wherein the particle system comprises an $Fe_3O_4$-transferrin dextran as well as other metal-transferrin dextran complexes wherein the metal is selected from the group comprising cobalt, zinc, chromium, nickel, gallium, platinum, manganese and rare earth metals such as dysprosium, erbium, europium, gadolinium, holmium, samarium, terbium, thulium, ytterbium and yttrium, other dimetallic compounds such as dysprosium-nickel, dysprosium-cobalt, gadolinium-iron, ytterbium-iron, cobalt-samarium, gadolinium-yttrium, and dysprosium-gallium actinide series elements and compounds. Additionally metalloporphyrin-transferrin wherein the metalloporphyrins are those mentioned above.

Further useful particle systems include antibody-ferritin-$Fe_3O_4$ complexes and other antibody-ferritin based systems where the $Fe_3O_4$ is optionally substituted with a transition metal, rare earth metal, metalloporphyrin or other ferromagnetic, diamagnetic or paramagnetic particle wherein the antibody is of monoclonal or polyclonal origin and is specifically reactive to the specific target organ or cell-type desired.

Metallothionein-based particle systems and lectin-based systems are also useful. In these systems either the metallothionein or lectin is used in combination with $Fe_3O_4$ or the transition metal, rare earth metal, metalloporphyrin and ferromagnetic, diamagnetic or paramagnetic particles as described above.

Specific metal-organic compound complexes are given in Table I.

TABLE I

PARTICLE COMPLEXES

Fe(III) Tetraphenylporphyrin sulfonate ($TPPS_4$) Acetate
Fe(III) $TPPS_4$ Acetate 4Na Salt ($H_2O$)
Fe(III) Mesoporphyrin IX Chloride
Fe(III) $TPPS_4$ Chloride
Co $TPPS_4$
Co(III) $MesoTPPS_4$ Tetra Na Salt (acetate)
Fe Phthalocyanine Tetrasulfonate Tetra sodium salt
Tetra Sodium-meso-Tetra (4-sulfonato-phenyl) Porphine (12 hydrate)
Fe(III) Tetra (N-Methyl 4-Puridyl) Porphyrin Pentachloride
Fe Phthalocyanine
Hemin
Fe-Hematoporphyrin D. (HPD)
Fe-Acetoxyethyl vinyl Deuteroporphyrin
Fe-Protoporphyrin IX
Fe-Deuteroporphyrin 2,4 bis acetal
Mn-$TPPS_4$
Co-$N^+$MTPyP
Mn-$N^+$MTPyP
Co-Mesoporphyrin X
Protohemin
Deuterohemin
Meso-tetra (4-N methyl pyridyl) hemin tetraiodide
Meso-tetra (4-carboxy phenyl) hemin

PARTICLE COMPLEXES

Ni-TPPS
Ni-HPD
Mn-Mesoporphyrin IX
Co-Protoporphyrin IX
Mn-Protoporphyrin IX
Sn-Protoporphyrin IX
Co-HPD
Mn-HPD
Gd-TPPS
Gd-HPD
Hematoporphyrin Mono-acetate-Fe Ferretin-Fe
Ferredoxin-Fe(4)
Transferrin-Fe
Hematoporphyrin Diacetate-Gd
$GdFe_2$-$TPPS_4$
$GdFe_2$-HPD
$FeTPPS_4(OH_2)_2ClO_4$
$FeTPP(OH_2)_2 ClO_4$
Bisimidozole $(FeTPPS)ClO_4$
Fe-nitrolacetate
Fetetrasulfinated phalocyanine
Rubrium-ferricytochrome/c The minute particles are to be injected or absorbed into the edges of the biological structures through the use of any suitable compatible liquid or solid vehicles. Aqueous solutions of any such body-acceptable materials as dextran, dextrose saline or blood as well as water alone can be used. Oil based materials may also be used. The particles can be in liquid suspension. Concentration of such body-acceptable materials that may be useful are those that are up to about 50% by weight in water. Solutions of 1% to 10% usually are adequate. The concentration of the particles in the solution is not critical and usually in a range between 10mg/cc to 200mg/cc of solution.

The solution of particle or particles themselves are applied to the edges of the biological structures to be connected. This may be done by passive means or by injection of the particles. The particles permeate all layers of the biological structure (i.e. the vessel wall). The time span for the application may vary depending on the various objectives. The time of application of the particles can precede the application of the alternating electromagnetic field by a period of 5 minutes to 24 hrs. or may occur immediately prior.

The depth of effect may be controlled by using different particle systems which permeate different layers of the vessel wall or by controlling the application to these layers and their extent. Consequently the type of connection which is formed can be controlled precisely.

The next stage of one aspect of the present invention is to bring about by inductive heating with an alternating electromagnetic field a transfer of energy to the particles and formation of the connection between the biological structures. The principle of inductive heating through hysteresis and eddy currents is a known principle.

The inductive heating of the minute particles is achieved by using an electronic oscillator operating in a frequency range which heats the particles by subjecting them to an intense frequency field with a helical coil, the field energy being converted to heat through hysteresis losses and the resistive dissipation of eddy currents. The helical inductive coil is of sufficient internal diameter to permit the biological structures to pass within and of such length to encompass the length of the connection. No minimum or maximum diameter is known to exist except that required from practical and economic considerations. As an example for coronary blood vessels the internal diameter may be 5-10mm. with a length of 2-4mm. The coil may be interrupted and only 180° to 330° instead of a full 360° to allow insertion of the vessel. The coil may also be composed of parts which fit together to surround the vessel and accomplish the same goal.

The frequency of the electromagnetic alternating frequency field will range from 1Hz to 10,000 megahertz and the power input of the oscillator generator from 0.5 kilowatts to 100 kilowatts. In this power and frequency range the coil is selected to produce from 400 to 800 oersteds preferably 550-650 oersteds.

The time necessary to inductively heat the minute particles in the edges of the biological structures to be connected depends substantially upon the frequency and the power producing the alternating electromagnetic field and ultimately the strength of the field produced. In general it has been found that a period of time 30 seconds to 10 minutes has been adequate to form the connection. It should be clearly understood that the variables with respect to the type and concentration of the particles in the vehicle and the electromagnetic treatment are not critical provided the necessary energy transfer is achieved.

EXAMPLE I

As a specific example of the simplest form of the present invention $Fe_3O_4$-dextran transferrin particles less than 1 micron in size are suspended in a 5% dextrose aqueous solution in an amount of 10 mg of particles per cc. The edges of the vessels to be connected are then exposed to this solution. After 2 minutes the biological structures are approximated in an inductive coil of 5mm. in diameter. The coil is connected to an alternating current generator producing a frequency of 400 kilohertz and a field of 600 oersteds. The biological structures are exposed to this alternating electromagnetic field for 30 seconds. The connection is then formed. If necessary 2-3 approximating sutures may be used to keep the vessels aligned.

While the simplest aspect of the invention has been described in detail, the selectivity of the particles for the edge of the biological structure may be enhanced by using antibodies to substances in the media of the vessel or through the use of the metalloporphyrin or porphyrin system. In addition microspheres of the ferromagnetic, paramagnetic or diamagnetic particles may contain collagen or material which helps bind the biological structures. Application of the alternating electromagnetic field releases these substances and enhances the strength of the connection.

An adhesive may be used which is applied with the particles and which is cured or activated by heating of the particles. It may also be desirable in some instances to use the adhesive without the particles. This addition of the adhesive can enhance the strength of the connection of the biological structures.

In addition particles and substances which currently exist and magnetic or electric dipoles which exist or are capable of being induced in the edges of the biological structures to be connected may be utilized. The alternating magnetic field interaction with the edges of the biological structures containing the particles acts to help oppose the edges.

The biological structure may consist of a vessel or an artery vein or lymphatic. Similarly the biological structure may be a portion of the gastrointestinal tract, the biliary system, tracheobronchial tract or urological system, as examples.

This method and composition of the present invention allow a mechanism for the delivery of energy in an even and uniform fashion to all layers of the biological structure thereby enhancing the connection which is formed. However different energy levels at different depths can be precisely controlled to produce different types of connections. This differential energy distribution can be controlled by using different energy levels to go to different depths, particles which go to different layers or which are placed in different layers, an alteration in the field strength, frequency, position of the coil or the length of time of exposure to the field.

The coil may be designed to be a fully encircling coil or only 90°-330° to allow easy access to the vessel. Similarly the coil can be made of pieces which are opposed around the vessel to produce the effect. A coil which is inside the vessel may be used to create the alternating electromagnetic field as well as in place of the external coil. In addition should it be desirable to alter the connection the alternating electromagnetic field can be applied to detach the biological structures and allow for changes in the connection.

The method and composition described in the present invention provide a means of connecting biological structures in a short period of time without producing trauma to the biological structures. In addition the entire connection can be created at once without the need for individual spot by spot fusion. There is no need to touch the biological structures and length is not used up as in eversion of the biological structure; hence tension is avoided. End to side connections are easily accomplished as are connections where a size discrepancy exists. No connectors or space for connections are required. All layers can be uniformly connected with equal energy deposition.

EXAMPLE II

A further specific example connects venous and arterial segments together by applying external electromagnetic energy. The end of the vessel to be joined is first exposed to a solution of $Fe_3O_4$ particle 10 mg/cc for a period of five minutes. The ends are then approximated and exposed to an alternating electromagnetic field at a frequency of 450 kilohertz for six minutes. A good connection is thereby formed which remains even after the field is removed. The connection should be able to withstand natural body movements and last indefinitely since once formed the normal endothelial cells should grow across the junction and in a short period of time the vessel wall will be essentially normal. Although the magnetic attraction of the particles is one aspect of the ability to form the connection, a major factor is the ability to transfer energy to the ends to be connected. The connection is formed by fusion of cellular components, not necessarily melted tissue, through the application of energy to the areas to be connected. By controlling the amount of energy to be delivered to the areas to be connected, the amount of tissue necrosis can be kept to a minimum. Even if some tissue alterations occur, the biological structures as in blood vessels have the ability to regenerate across the connection to form a normal connection.

Another method of forming this biological connection is to expose the two portions of tissue to be connected to a material which can be activated by light or other wavelengths. The wavelengths chosen can be determined by the agent(s) used. An example is in the use of porphyrins, metalloporphyrins, chlorins, chlorinporphyrin esters, hematoporphyrin derivative, merocyanine 540 or other substances capable of accepting energy transfer on exposure to light or other forms of radiation.

EXAMPLE II

A further specific example connects vascular segments together by applying external energy in the visible range. The ends of the vessels to be joined are first exposed to a solution of Chlorinporphyrin ester 2.5mg/cc for a period of three minutes. The ends are then approximated and exposed to a light either uniform or laser induced at a wavelength of 640nm for a period of four minutes. A good connection is then formed which remains after the light is removed. The connection should be able to withstand natural body movements and last indefinitely since once formed the normal endothelial cells should grow across the junction and in a short period of time the vessel wall will be essentially normal. A major factor is the ability to transfer energy to the ends to be connected. The connection is formed by fusion of cellular components, not necessarily melted tissue, through the application of energy to the areas to be connected. By controlling the amount of energy to be delivered to the areas to be connected, the amount of tissue necrosis can be kept to a minimum. Again even if some tissue alterations occur, the biological structures as in blood vessels have the ability to regenerate across the connection to form a normal connection.

From the foregoing detailed description it will be evident that there are a number of changes, adaptations and modifications of the present invention which come within the province of those persons having ordinary skill in the art to which the aforementioned invention pertains. However, it is intended that all such variations not departing from the spirit of the invention be considered as within the scope thereof as limited solely by the appended Claims.

I claim:

1. A process for the connection of biological structures in living tissue by the application of external electromagnetic energy capable of the generation of heat and the alteration of biophysical properties in the edges of biological structure comprising:
   introducing into the edges of the biological structures minute ferromagnetic paramagnetic, or diamagnetic particles capable of being inductively heated, said particles being absorbed therein approximating said edges,
   subjecting the edges of the biological structures to an alternating electromagnetic field to inductively heat and alter the biophysical properties of the minute particles and thereby the edges of the biological structures, and
   continuing the inductive energy transfer of said particles to form the connection of the edges of the biological structures to form a unit.

2. The process of claim 1 wherein the particles are selected from the group comprising ferromagnetic, paramagnetic and diamagnetic elements, inorganic compounds, organic compounds and combinations thereof including ferric hydroxide (FeOOH), iron oxide, Fe-dextran transferrin, ferrofluids, metalloporphyrins, porphyrins, and combinations thereof.

3. The process of claim 2 wherein said elements and inorganic compounds are selected from the group comprising cobalt, zinc, chromium, nickel, platinum, rare earth such as dysprosium, erbium, europium, gadolinium, holmium, samarium, terbium, thulium, ytterbium, yttrium and compounds thereof such as dysprosium sulfate, erbium sulfate, europium oxide, europium sulfate, gadolinium oxide, gadolinium sulfate, holmium oxide, samurium sulfate, terbium sulfate, thulium oxide, ytterbium sulfide, yttrium oxide, yttrium sulfate, yttrium ferrioxide ($Y_3Fe_5O12$), yttrium aluminum oxide ($Y_3Al_5O_{12}$), dysprosium-nickel, dysprosium-cobalt, gadolinium-iron, ytterbium-iron, cobalt-samarium, gadolinium-ytterbium, dysprosium-gallium, and actinide series elements and compounds thereof.

4. The process of claim 2 wherein said organic compounds are selected from the group comprising:
(a) dextran metal complexes wherein said metal is selected from the group including cobalt, zinc, chromium, gallium, manganese, nickel, platinum, dysprosium, erbium, europium, gadolinium, bolmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium, and iron such as $Fe_2O_3$ particles, $Fe_3O_4$ particles and FeOOH particles and $Fe_2O_3$dextran complexes, $Fe_3O_4$-dextran complexes, and FeOOH-dextran complexes;
(b) iron transporting and chelating compounds comprising ferric ammonium citrate, enterochelin, transferrin, metallothionein, hydroxamates, phenolates, ferrichromes, desferriferrichromes, ferritin, ferric mycobactins and iron sulfur proteins such as ferredoxin and rubredoxin;
(c) porphyrins comprising etioporphyrins, mesoporphrins, uroporphyrins, coproporphyrins, protoporphyrins, dicarboxylic acid containing porphyrins, substituted porphyrins such as tetraphenylporphyrin sulfonate and protoporphyrin containing molecules such as hematoporphyrins, chlorophylls, and cytochromes; and combinations thereof.

5. The process of claim 4 wherein the natural occurring metal moiety of said porphyrin is optionally substituted with a metal selected from the group comprising cobalt, zinc, chromium, gallium, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium.

6. The process of claims 4 or 5 wherein said iron transporting, iron chelating and porphyrin compounds are chemically complexed with dextran.

7. The process of claim 6 wherein said composition is chemically complexed with an antibody.

8. The process of claim 1 wherein the particles are directly applied to the edge of the biological structure and/or injected in the edge.

9. The process of claim 1 including the use of a localized field to localize the particles in the edge of the biological structure.

10. The process of claim 1 wherein the edges of the biological structures are opposed by the use of magnetic material encircling the edges.

11. The process of claims 1, 2, 8, 9 or 10 as applied to blood vessels, arteries, veins, lymph sites, the gastrointestinal tract, the respiratory system, the biliary system or the gentourinary system.

12. The process of claims 1, 2, 8, 9 or 10 including supplying an even distribution of energy to the edges of the biological structure.

13. The process of claims 1, 2, 8, 9 or 10 where different particles which go to or are injected to different depths are utilized to form the connection.

14. The process of claims 1, 2, 8, 9 or 10 including utilizing different energy levels to specifically control the type of connection between the biological structures.

15. The process of claim 1 including using outside coil to create the alternating electromagnetic field.

16. The process of claim 1 including using a coil inside the biological structure to create the alternating electromagnetic field.

17. The process of claims 1, 2, 8, 9, 10, 15 or 16 including using magnetic or electric dipoles already present in the biological structures or capable of being induced in the edges of the biological structures to help form the connection.

18. The process of claims 1, 2, 8, 9, 10, 15 or 16 where alteration in field strength, position of the coil, frequency number of particles and/or length of time of exposure is used to affect the energy level in the connection of the biological structures and thereby affect the connection.

19. The process of claims 1, 2, 8, 9, 10, 15 or 16 where the particles are injected 5 minutes to 24 hours prior to treatment with the alternating electromagnetic field and/or just prior to treatment.

20. The process of claims 1, 2, 8, 9, 10, 15 or 16 where the alternating electromagnetic field is produced by a coil which covers 90 degrees–330 degrees of the full 360 degrees to provide easy access to the edges of the biological structures.

21. The process of claims 1, 2, 8, 9, 10, 15 or 16 where the coil used to produce the electromagnetic field is formed of parts which may be approximated around the edges of the biological structures to form the connection.

22. The process of claim 1 wherein the particles consists of a microsphere coated with a ferromagnetic, paramagnetic or diamagnetic substance containing collagen or a material which enhances the binding of the biological structures and with the application of an alternating electromagnetic field releases these materials and enhances the connection of the biological structures.

23. The process of claims 1, 2, 8, 9, 10, 15, 16 or 23 where an adhesive is applied to the biological structures, with or without the particles, to enhance the connection of the biological structures.

24. The process of claim 23 where said adhesive is activated by an alternating electromagnetic field to enhance the connection of the biological structures.

25. The process of claim 2 as applied to blood vessels, arteries, veins, lymph sites, the gastrointestinal tract, the respiratory system, the biliary system or the gentourinary system, and including supplying an even distribution of energy to the edges of the biological structure.

26. The process of claim 25 where different particles which go to or are injected to different depths are utilized to form the connection.

27. The process of claim 26 where different energy levels are utilized to specifically control the type of connection between the biological structures.

28. The process of claim 1 where magnetic or electric dipoles already present in the biological structures or capable of being induced in the edges of the biological structures are used to help form the connection,
where alteration in field strength, position of the coil, frequency, number of particles and/or length of time of exposure is used to affect the energy level in the connection of the biological structures and thereby affect the connection and
where the particles are injected 5 minutes to 24 hours prior to treatment with the alternating electromagnetic field and/or just prior to treatment.

29. The process of claim 28 where the alternating electromagnetic field is produced by a coil which covers 90 degrees to 330 degrees of the full 360 degrees to provide easy access to the edges of the biological structures.

30. The process of claim 28 where the coil is formed of parts which may be approximated around the edges of the biological structures to form the connection.

31. A process for the connection of biological structures in living tissue comprising:
introducing into the edges of the biological structures minute particles each of less than approximately ten microns and capable of being inductively heated when subjected to a high frequency alternating electromagnetic field, approximating said edges
subjecting said edges of said biological structures to a high frequency alternating electromagnetic field to inductively heat and alter the biophysical properties of said minute particles and thereby the edges of said biological structures, and
continuing the inductive energy transfer of said particles to form the connection of the edges of said biological structures to form a unit.

32. The process of claim 31 including,
said introducing including said particles being passively absorbed.

33. The process of claim 31 including,
said introducing including directly injecting said particles into said edges.

34. The process of claim 31 including,
said particles being ferromagnetic, paramagnetic, or diamagnetic.

35. The process of claim 31 including,
said subjecting step commencing after the completion of said introducing step.

36. The process of claim 31 including,
said subjecting step commencing after the start of said introducing step.

37. The process of claim 31 including,
said subjecting including said high frequency alternating field having a frequency of 400 kilohertz.

38. The process of claim 31 including,
said introducing including said particles being less than one micron size.

39. The process of claim 31 including,
said introducing including said particles being one micron to seven microns in size.

40. The process of claim 31 including,
said continuing including said biological structures being arteries.

41. The process of claim 31 including,
said biological structures being blood vessels.

42. The process of claim 41 including,
said particles being adapted to specifically localize in the layers of the vessel wall of said blood vessels.

43. The process of claim 41 including,
said introducing including said minute particles selectively localizing in the layers of the blood vessel wall.

44. The process of claim 31 including,
said biological structures comprising lymphatics.

45. The process of claim 31 including,
said subjecting including raising the energy level of said minute particles in the areas to be connected to form the connection.

46. The process of claim 31 including,
applying an adhesive to said biological structures to enhance the connection of said biological structures.

47. The process of claim 46 including,
activating said adhesive by an alternating electromagnetic field to enhance the connection of said biological structures.

48. The process of claim 31 including,
said particles being adapted to accumulate intracellularly, and
said introducing including intracellularly introducing said particles into said biological structures.

49. A process for the connection of biological structures in living tissue comprising:
introducing into the edges of the biological structures minute particles capable of being activated by an external light source, approximating said edges,
subjecting said edges of the biological structures to electromagnetic radiation to alter the biophysical properties of said minute particles and thereby said edges of the biological structures, and
continuing the energy transfer of said particles to form the connection of the edges of the biological structures to form a unit.

50. The process of claim 49 including,
said subjecting including said electromagnetic radiation being light.

51. The process of claim 49 including,
said subjecting including laser generating said electromagnetic radiation.

52. The process of claim 49 including,
said introducing including said particles being selected from the group of prophyrins, metalloporphyrins, hematoporphyrin derivatives, chlorinporphyrin esters, chlorins, and merocyanine 540.

53. The process of claim 49 including,
said introducing said particles being ferromagnetic, paramagnetic or diamagnetic.

54. The process of claim 49 including,
said introducing including injecting said particles into said edges.

55. The process of claim 49 including,
said introducing including said biological structures being selected from the group of blood vessels, arteries, veins, lymph sites, the gastro-intestinal tract, the respiratory system, the biliary system, and the gentourinary system.

56. The process of claim 49 including,
said subjecting including subjecting said edges to light to alter the biophysical properties of said minute particles and thereby said edges of the biological structures.

57. The process of claim 49 including,
said introducing including said particles being passively absorbed.

58. The process of claim 49 including,
said subjecting including supplying an even distribution of energy to said edges of the biological structures.

59. The process of claim 49 including,
said subjecting including utilizing different energy levels to control the type of connection between the biological structures.

60. The process of claim 49 including,
applying an adhesive to the biological structures to enhance the connection of the biological structures.

61. The process of claim 60 including, said applying step being before said introducing step.

62. The process of claim 60 including,
said applying step commencing after said introducing step.

63. The process of claim 60 including,
activating said adhesive by an alternating electromagnetic field.

64. The process of claim 49 including,
said subjecting including said electromagnetic radiation being in the visible range.

65. The process of claim 49 including,
said introducing including directly applying said particles to said edges.

66. The process of claim 49 including,
said subjecting including said electromagnetic radiation having a wavelength 100–1100 nm.

67. The process of claim 49 including,
before said subjecting, generating said electromagnetic radiation with a laser.

68. The process for the connection of biological structures in living tissue comprising:
introducing into the edges of the biological structures minute particles capable of being inductively heated approximating said edges,
subjecting the edges of the biological structures to an alternating electromagnetic field to inductively heat and alter the biophysical properties of said minute particles and thereby said edges of the biological structures, and
continuing the inductive energy transfer to said particles to form the connection of the edges of the biological structures to form a unit.

69. The process of claim 68 including,
said introducing including injecting said particles directly into said edges.

70. The process of claim 68 including,
said introducing including said particles being ferromagnetic, paramagnetic or diamagnetic.

* * * * *